Sept. 28, 1943. C. L. DUNN ET AL Re. 22,379
RECOVERY OF PURE AROMATICS
Original Filed July 27, 1940
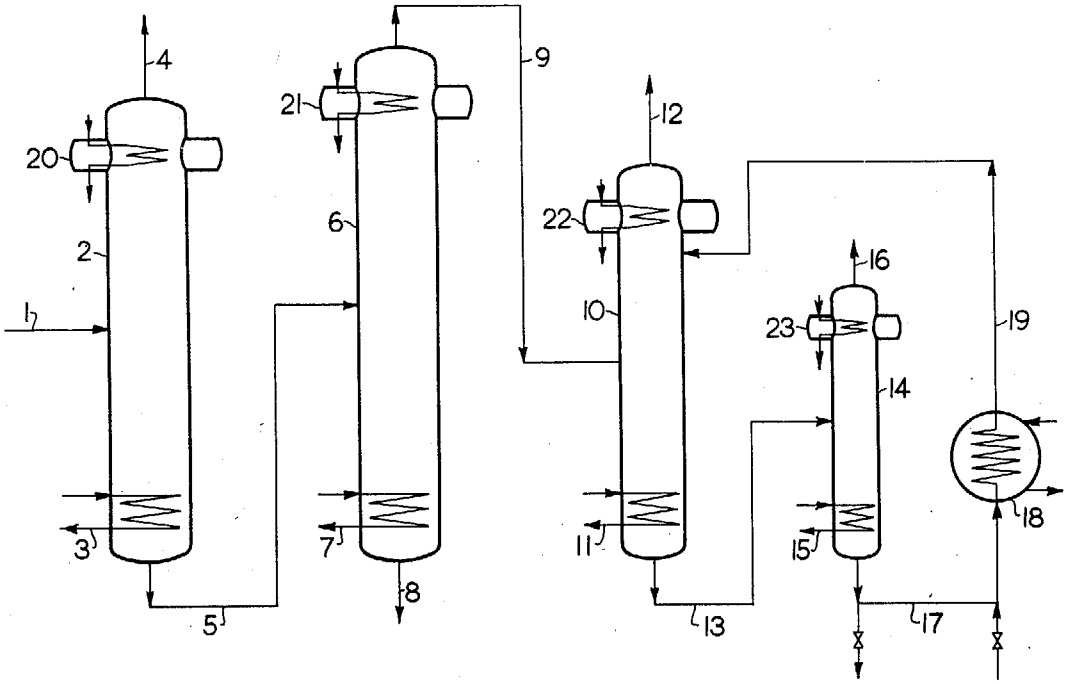
Inventors: Clarence L. Dunn
Robert B. McConaughy
By their Attorney: [signature]

Reissued Sept. 28, 1943 Re. 22,379

UNITED STATES PATENT OFFICE 22,379

RECOVERY OF PURE AROMATICS

Clarence L. Dunn, Berkeley, and Robert B. McConaughy, El Cerrito, Calif., assignors to Shell Development Company, San Francisco, Calif., a corporation of Delaware Original No. 2,288,126, dated June 30, 1942, Serial No. 348,046, July 27, 1940. Application for reissue October 19, 1942, Serial No. 462,479½

10 Claims. (Cl. 260—674)

This invention relates to a process for the separation of pure aromatic hydrocarbons such as benzene, toluene, paracymene, naphthalene or mixtures of aromatic hydrocarbons of identical molecular weight, such as xylenes and ethyl benzene, or the isomeric methyl naphthalenes and the like from petroleum hydrocarbon distillates. More particularly, it deals with a process wherein a distillate containing the desired aromatic constituent is fractionated to produce a concentrate containing an increased proportion of the aromatic constituent to be separated and said concentrate is subjected to an extractive distillation or a vapor phase extraction to produce the substantially pure aromatic constituent.

It has long been recognized that petroleum contains a vast number of hydrocarbons and among those minor quantities of aromatic compounds, both the simple relatively low-boiling aromatics such as benzene, toluene, ethyl benzene, xylenes, etc., as well as the relatively high-boiling condensed ring compounds such as naphthalenes, phenanthrenes and the like.

These individual hydrocarbons are present in such variety and low concentration each that heretofore it has not been possible to separate them except by expensive, tedious processes in the laboratory, and in many instances it has been impossible to isolate individual compounds in any known manner.

It is known that aromatic compounds, for example, toluene occurring in small quantities in petroleum hydrocarbons cannot usually be concentrated by fractional distillation to produce concentrates containing more than about 20% toluene. Further concentration of toluene by fractional distillation is, however, impossible because of the existence of minimum boiling azeotropic mixtures formed by toluene with some of the other hydrocarbons in the mixture. Therefore, toluene, for instance, of a sufficiently high degree of purity to meet nitration requirements cannot be produced from petroleum distillates by fractional distillation alone.

It is an object of our invention to recover commercially substantially pure aromatic hydrocarbons or mixtures of aromatic hydrocarbons having the same molecular weight such as benzene, toluene, xylenes and ethyl benzene, paracymene, naphthalene, isomeric methyl naphthalenes and the like from petroleum distillates. Another purpose is to provide a process whereby substantially all of the small amounts of these compounds which are normally present in petroleum distillates can be recovered economically. It is a further object to produce from petroleum fractions aromatic hydrocarbons of high purity, for example, benzene or toluene of sufficiently high purity to meet nitration specifications; and it is another object to produce these compounds in a substantially pure state by employing only physical processes.

We have discovered that it is commercially possible by the method of our invention to produce from petroleum distillates compounds of high purity. Our method comprises producing first a concentrate of the aromatic constituent to be extracted having specific properties and then subjecting this concentrate to a vapor phase extraction or extractive distillation in the presence of a relatively high-boiling selective solvent which has preferential solvent power for the aromatics to be extracted. In the extraction step, the non-aromatic hydrocarbons are taken overhead while the aromatic is withdrawn from the bottom of the extraction zone with the solvent from which it is readily separated by simple distillation.

The following discussion of the production of toluene of high purity by the method of our invention serves to illustrate it in its essentials. As already stated, toluene (as well as other aromatic hydrocarbons) forms azeotropes with aliphatic and naphthenic hydrocarbons having boiling temperatures close to (both below and above) the boiling temperature of toluene. Because of the distortion of boiling range caused by these azeotropes which boil below the normal boiling temperatures of the toluene and these aliphatic or naphthenic hydrocarbons, it is impossible to exclude non-toluene hydrocarbons from the first concentrate. This fact is illustrated by the following example:

An East Texas gasoline having an A. S. T. M. boiling range from 42° to 133° C. and containing 1.52% toluene was separated by precision distillation into narrow fractions, each of which had a 10° C. "true" boiling range. A fraction thus produced, having a "true" boiling range from 95° to 105° C., contained approximately 65% of all the toluene (boiling point 110.6° C.), and the next higher boiling fraction boiling from 105° to 115° C. contained most of the remainder of the toluene. Thus, the concentrate containing substantially all, i. e., at least about 90%, of the toluene contained in the gasoline distillate had a true boiling range from 95° to 115° C.

Generally speaking, it has been found that the true boiling range of suitable concentrates ranges from below 101° C. to above 112° C., if substantially all the toluene is to be recovered with practical reflux ratios. If toluene is removed from the concentrate, as by chemical means, the remaining non-toluene hydrocarbons usually have a true end boiling point substantially above 115° C.

For our purpose, we have found that it is sufficient to produce a toluene concentrate containing not less than about 5% and preferably at least about 10% toluene, the remainder being non-toluene hydrocarbons, of which the components boiling above 120° C. and preferably above 115° C. must not exceed the toluene content and the amount of components boiling above 125° C. being not greater than the larger of the following limitations:

1. 5% of the toluene content, or
2. ½% of the total concentrate

In determining the contents of relatively high-boiling compounds of the concentrate, the ASTM distillation is insufficiently accurate, and therefore is not applicable. Instead, it is necessary to determine these contents by first removing all of the aromatics, as by sulfonation or nitration, preferably in the presence of suitable catalyst such as silver sulphate. The non-aromatic hydrocarbon residue is then subjected to analytical batch distillation, preferably carried out in a still equipped with a column equivalent to at least 30 equilibrium plates, using a reflux ratio of at least 20:1. The still-head temperatures are then read as the "true" boiling points.

The inclusion in the concentrate of non-aromatic hydrocarbons boiling lower than toluene has little effect on the subsequent production of high purity toluene, except that their presence in excessive amounts tends to dilute the toluene and thereby increase the loss of toluene in the extractive distillation step. Quantities of high-boiling hydrocarbons in excess of those specified above preclude the production of 1° toluene.

The importance of the 5% lower limit for the toluene content in the concentrate is well illustrated by the following explanation: Consider an extractive distillation column to which is fed the concentrate and from which a solution of nitration grade toluene in a selective solvent is withdrawn at the bottom, while non-toluene hydrocarbons are taken overhead. In purifying the toluene to the required degree, the greatest difficulty resides in preventing the relatively high-boiling non-toluene constituents from contaminating the bottom product. Since the presence of these high-boiling constituents in the feed is unavoidable for the reasons explained above, and since, moreover, an absolutely perfect separation of toluene from the non-toluene hydrocarbon is impracticable, if not impossible, because of the difficulty of controlling temperatures, feed and product rates, etc., it follows that at least a small amount of the toluene must go overhead together with the non-toluene vapors. It has been found in practice that the toluene concentration in the vapors passing overhead is at least from ½% to 2%. If the concentration of the toluene in the feed is 5%, then on the basis of 100 barrels of feed to the column, 5 barrels are toluene. 95 barrels of non-toluene hydrocarbons must pass overhead, and in addition, the ½% to 2% toluene which they contain. Approximately 0.42 to 1.9 barrels, or an average of about 1.2 barrels, of toluene are thus taken overhead. This amounts to a loss of toluene of about 24% of the total theoretically recoverable amount.

If one now considers the case where the feed contains 4% toluene only, then the loss of toluene rises to about 30%; and if the toluene content of the feed is 2% or less, substantially no pure toluene can be recovered.

For the above calculations, the most favorable operating conditions have been assumed that can be maintained with conventional control equipment and recoveries of pure toluene may be considerably lower than indicated. This clearly shows why it is necessary to have a minimum amount of about 5% toluene in the concentrate in order to carry out the process successfully on a commercial scale.

The extractive distillation step may be carried out in the conventional manner wherein a selective solvent is caused to run down the distillation column, as the mixed vapors comprising the toluene ascend. The column may be of the packed or bubble plate type. The selective solvent scrubs the mixed vapors in the enriching zone, removing the toluene preferentially from the vapors, thereby forming a fat solvent. This fat solvent contains some quantities of non-toluene hydrocarbons which are removed from the solvent in the stripping zone as it passes down the column, by contact with ascending toluene vapors to give a fat solution consisting substantially only of toluene and solvent.

The attached drawing represents a flow diagram of a simplified apparatus suitable for carrying out our invention. A straight-run gasoline distillate, such as is produced in ordinary oil refining practice, preferably having a narrow A. S. T. M. boiling range from below about 90° C. to above about 125° C. and containing a small amount of toluene is fed continuously through line 1 to a precision fractionation column 2 equipped with reboiler 3 and partial condenser 20. As large a portion as is practical of the hydrocarbons lighter than toluene is taken overhead by way of line 4, care being taken that substantially no toluene goes with it. The bottoms from column 1, still containing all the toluene, pass via line 5 to a second precision fractionation column 6 having at its bottom reboiler 7 and partial condenser 21. This column is operated in a manner so that substantially all of the oluene is vaporized and taken overhead, while as much as possible of the higher boiling non-toluene hydrocarbons are removed as bottoms through line 8. By maintaining the proper operating conditions in columns 2 and 6, it is usually possible to produce from column 6 overhead vapors which contain at least 5% toluene and whose content of components boiling above 120° C. is not greater than its toluene content. These vapors pass through line 9 to extractive distillation column 10, wherein they are contacted with a selective solvent for aromatics, such as alkyl phenols, admitted through line 19, to a point below the top of column 10, the portion of the column above the point of admission and partial condenser 22 serving to prevent loss of solvent with the non-toluene hydrocarbons leaving through line 12. The solvent flows downward in countercurrent to the ascending vapors thereby scrubbing the toluene from the vapors by reason of its selective solvent power for aromatics. Non-toluene hydrocarbon vapors leave column 10 through overhead line 12. In reboiler 11, disposed at the bottom of column 10, small amounts of dissolved non-toluene hydrocarbons are driven out from the descending solution, resulting in a fat solvent consisting substantially only of toluene and solvent. This fat solvent is withdrawn through line 13, whence it passes through distillation column 14 equipped with reboiler 15 and partial condenser 23. In column 14 the toluene is distilled, resulting vapors going through line 16 to storage not shown. The selective solvent thus freed from toluene emerges from column 14 through bottom line 17 and passes through cooler 18. The cooled selective solvent returns to the top of column 10 for use in another extraction cycle.

For simplicity, the drawing does not show pumps, heat exchangers, valves, by-passes, and other auxiliaries, the proper placement of which will be at once evident to those skilled in the art.

While in the above, our invention has been described in detail with particular reference to the separation of toluene from petroleum distillates which contain toluene naturally associated therewith, it is not limited thereto. Thus, it may be applied as well to the separation of other pure aromatics or mixtures of isomeric aromatic, which may be contained in straight-run, cracked or other petroleum distillates, the boiling range of which embraces the boiling temperatures of these aromatics. Further, while our process is particularly applicable to the treatment of petroleum fractions containing relatively low percentages of aromatics, it has also been successfully applied to the production of pure aromatics from fractions containing aromatics in relatively high concentrations. It is only necessary that the concentrate taken for extractive distillation be prepared on the basis of the same general principles as those used in producing the toluene concentrate and that the solvent employed in the extractive distillation have a boiling temperature sufficiently above the boiling temperatures of the aromatic constituent to be separated so that the two can be readily separated from each other by simple fractional distillation. Also, it is desirable that the solvent should boil sufficiently above the boiling temperature of the highest boiling constituent of the concentrate so that there is substantially no loss of solvent to the residual non-toluene hydrocarbon vapors. The solvents must also be chemically and thermally stable under the conditions of the extraction or extractive distillation.

Examples of solvents which are suitable for the concentration of the various aromatics in the extractive distillation step are phenol, cresylic acids, alkyl phenol mixtures, aniline, alkyl anilines, diphenyl amine, ditolyl amines, carbitols (diethylene glycol mono ethers) such as methyl, ethyl, propyl carbitols, chlorinated dialkyl ethers such as beta-beta-dichlor ethyl ether, nitrobenzene, nitrotoluene, nitroxylenes, naphthols, alkyl naphthols, benzo phenone, phenyl tolyl ketone, diphenylene ketone, alkyl phthalates, such as dimethyl phthalate, alkyl salicylates such as methyl salicylate, benzyl alcohol, benz chlorides, i. e., benzyl, benzal, benzo chlorides, benzonitrile, diphenyl oxide, ditolyl oxide, hydroxy pyridine, nitropyridine, chlorinated pyridines, quinoline, isoquinoline, chlorinated quinoline, hydroxy quinolines, 5-nitro quinoline, tetra hydro furfuryl alcohol, furfural alcohol, furfural, the mono glycerol ethers such as 1-methoxy glycerol, 2-methoxy glycerol, 1-ethoxy glycerol, 2-ethoxy glycerol, 1-propoxy glycerol, 2-propoxy glycerol, 1-isopropoxy glycerol, 2-isopropoxy glycerol; the glycerol di-ethers such as 1,2-di-methoxy glycerol, 1,3-di-methoxy glycerol, 1,2-di-ethoxy glycerol, 1,3-di-ethoxy glycerol, 1,2-dipropoxy glycerol, 1,3-dipropoxy glycerol, 1,2-di-isopropoxy glycerol, and 1,3-di-isopropoxy glycerol; the mixed diglycerol ether esters such as 1-ethoxy, 2-methoxy glycerol, 1-methoxy, 3-propoxy glycerol, 1-ethoxy, 2-isopropoxy glycerol.

While the majority of the above-listed solvents can be used for the separation of the lower boiling aromatics in the extractive distillation step, only the higher boiling members can be employed for the separation of the higher boiling aromatics for the reasons outlined above which serve as a guide for the selection of any specific solvent for a given base. It is to be emphasized that the solvents listed above are intended as examples only and on the basis of our disclosures other equivalent solvents will be at once evident to those skilled in the art.

In separating a given concentrate into its toluene and non-toluene components, the number of plates in the extractive distillation column required with a given reflux, or conversely, the amount of reflux required with a given number of plates, decreases as the amount of solvent employed relative to the amount of concentrate treated increases. The amount of solvent necessary increases with the boiling point of the highest boiling non-toluene components present; however, we have found that one to three parts by weight of solvent to one part by weight of concentrate are usually sufficient. Less solvent may be employed with concentrates which contain only low-boiling non-toluene components, and more solvent if the concentrate contains a large amount of toluene, as the solution of toluene and solvent obtained as the bottom product of column 10 will then not be inconveniently low.

For the successful operation of our process it is necessary that the concentrate which is to be extractively distilled have the following general properties. It should contain at least 5% and preferably not less than about 10% by weight of the aromatic to be extracted. It should have a true initial boiling point at least 10±½° C. lower than the boiling temperature of the pure aromatic or the lowest boiling member of a group of aromatic isomers, and a true final boiling point at least 2±½° C. higher than the boiling temperature of said aromatic or the highest boiling member of a group of aromatic isomers. Thus, the boiling point of pure toluene being 110.6° C., the concentrate to be extracted should at least encompass the true boiling range indicated earlier from below 101° C. to above 112° C.

In cases where a group of isomers boil over a considerable range, it is possible to get a separation between isomers by careful control of the boiling range of the concentrate so as to exclude either lower or higher boiling members of the isomeric group from the concentrate being extractively distilled. It is difficult to separate isomers in the extractive distillation step since the common selective solvents generally show practically no difference in solvent selectivity for different isomers of the type, e. g., ortho, meta or para xylene.

In addition, the concentrate must not contain an amount of components boiling higher than 10±½° C. above the boiling point of the aromatic to be extracted or the highest boiling member of a group of isomers, which amount is greater than the content of this aromatic, nor a content of components boiling higher than 15±½° C. above the boiling point of said aromatics or highest boiling member of a group of isomers, being larger than the following limitations: (1) 5% of the toluene content, or (2) ½% of the total concentrate. The following table gives examples showing the properties of suitable concentrates for the production of various pure aromatics:

*Table*

| Aromatic to be separated | Boiling point of aromatic to be separated | Properties of fraction to be extractively distilled | | |
|---|---|---|---|---|
| | | Content of components boiling above temp. shown must be not greater than content of aromatics | Content of components boiling above temp. shown must not be greater than 5% of content of aromatic of ½% of the total concentrate | Min. boiling range °C. from below to above |
| | °C. | °C. | °C. | °C. |
| Benzene | 80 | 90 | 95 | 73–384 |
| Toluene | 110.6 | 120 | 125 | 100–112 |
| o-Xylene | 144 | | | |
| m-Xylene | 139 | | | |
| p-Xylene | 138 | 154 | 159 | 127–147 |
| Ethyl benzene | 136 | | | |
| p-Cymene | 176 | 186 | 191 | 167–179 |
| Naphthalene | 218 | 228 | 233 | 209–221 |

The above examples illustrate the general principles to be applied for the separation of a given aromatic hydrocarbon or a mixture of isomeric aromatic hydrocarbons from hydrocarbon distillates of relatively wide boiling ranges. By following these principles aromatic hydrocarbons not enumerated may be separated from hydrocarbon mixtures without departing from the spirit of the present invention.

The extractive distillation may be carried out adiabatically or isothermally. In the latter case, the stripping and enriching zones are operated at substantially the same temperature. If desired separation may be made under either reduced or elevated pressure. When operating under reduced pressure, it is sometimes possible to employ selective solvents which would not otherwise be applicable because of their tendency to undergo chemical changes at elevated temperatures.

If the distillate to be treated contains certain sulphur compounds, for example, methyl thiophene, which commonly occurs in cracked gasolines and which are apt to contaminate the aromatics due to their relatively high solubility in selective solvents for aromatics, these objectionable compounds may be removed prior to treatment by our process, or if preferred, may be removed from the aromatic fraction subsequent to its having been isolated.

Our process for the production of pure aromatics is also applicable to hydrocarbon oils other than petroleum oils which comprise mixtures of aromatics with non-aromatics, i. e., aliphatic, alicyclic, or both hydrocarbons, provided they contain hydrocarbons of the different types that boil sufficiently close to each other to form azeotropes during distillation. Examples of such mixtures are certain coal tar distillates, synthetic hydrocarbon mixtures such as may be obtained by cyclization of aliphatics, or dehydrogenation of naphthenes, etc.

*Example*

A straight-run California gasoline distillate boiling from 70° C. to 130° C. was fractionally distilled in a precision distillation column equivalent to 50 plates to produce a concentrate boiling between 98° C. and 120° C. containing 17.8% toluene. The concentrate was fed continuously in the vapor state to a packed column equipped with reboiler having an efficiency equivalent to 44 theoretical plates. The ratio of reflux to take-off at the still-head was 2 to 1. The temperatures at the top and bottom of the column were 102.5° and 158° C., respectively. Aniline was fed to the upper part of the column as a selective solvent. The aniline feed was 1.3 compared to 1 for the concentrate feed.

The top product contained 98.9% non-toluene hydrocarbons, a little over 1% toluene and substantially no aniline. The bottom product consisted of 11.6% toluene in aniline with less than 0.2% non-toluene hydrocarbons. Distillation of this bottom product at a 3 to 1 reflux ratio in a batch still equivalent to eight theoretical plates gave toluene of better than 98% purity, meeting specifications for nitration grade. The bottom aniline product was suitable for re-use in the extractive distillation column. The toluene recovery was 95% of the total toluene content contained in the original distillate.

We claim as our invention:

1. In a process for separating a substantially pure aromatic fraction consisting essentially of aromatics of identical molecular weight from a hydrocarbon mixture containing non-aromatic hydrocarbons and having a relatively wide boiling range above and below the boiling temperatures of said aromatics, the steps of fractionally distilling said mixture to produce a concentrate containing not less than about 5% of said aromatic fraction, said concentrate containing an amount of components boiling higher than about 10° C. above the upper boiling temperature limit of said aromatic fraction, which amount is not greater than the content of said aromatic fraction in said concentrate, and a content of components boiling higher than about 15° C. above said upper boiling temperature limit which content is not greater than the larger of the following; 5% of said content of said aromatic fraction and ½% of the total concentrate, contacting said concentrate in the vapor phase with a liquid solvent selectively dissolving aromatic hydrocarbons to produce a residual vapor and a fat solvent containing absorbed vapors consisting essentially of aromatic hydrocarbons, separating said fat solvent from said residual vapor, and fractionally distilling the separated fat solvent to recover said absorbed aromatics, said solvent boiling at a temperature substantially above the said highest boiling temperature of said pure aromatic fraction.

2. The process of claim 1 wherein the hydrocarbon mixture is a petroleum distillate.

3. In a process for separating a substantially pure aromatic fraction consisting essentially of aromatic hydrocarbons of identical molecular weight having at least 7 carbon atoms from a petroleum hydrocarbon distillate containing non-aromatic hydrocarbons and having a relatively wide boiling range above and below the boiling temperatures of said aromatics, the steps of fractionally distilling said distillate to produce a concentrate containing not less than about 5% of said aromatic fraction, said concentrate containing an amount of components boiling higher than about 10° C. above the upper boiling temperature limit of said aromatic fraction, which amount is not greater than the content of said aromatic fraction in said concentrate, and a content of components boiling higher than about 15° C. above said upper boiling temperature limit which is not greater than the larger of the following: 5% of said content of said aromatic fraction and ½% of the total concentrate, said concentrate having a true initial boiling point at least about 10° C. below the lowest boiling temperature of said pure aromatic fraction and a true final boiling point at least about 2° C. above the highest boiling temperature of said pure aromatic fraction, contacting said concentrate in the vapor phase with a liquid solvent selective for aromatics, to produce a fat solvent containing absorbed aromatics only and a residual hydrocarbon vapor, separating said fat solvent from said vapor, and fractionally distilling the separated fat solvent to recover said absorbed aromatics, said solvent boiling at a temperature substantially above the said highest boiling temperature of said pure aromatic fraction.

4. In a process for separating a substantially pure aromatic fraction consisting essentially of xylenes and ethyl benzene from a petroleum hydrocarbon distillate containing non-aromatic hydrocarbons and having a relatively wide boiling range above and below the boiling temperatures of said xylenes and ethyl benzene, the steps of fractionally distilling said distillate to produce a concentrate containing not less than about 5% of said xylenes and ethyl benzene, said concentrate containing an amount of components boiling higher than about 154° C. not greater than the content of said xylenes and ethyl benzene in said concentrate, and a content of components boiling higher than about 159° C. not greater than the larger of the following: 5% of said content of said xylenes and ethyl benzene content and ½% of the total concentrate, said concentrate having a true initial boiling point not higher than 127° C. and a true final boiling point of at least 147° C., contacting said concentrate in the vapor phase with a liquid solvent selectively dissolving aromatic hydrocarbons and having a boiling temperature substantially above 144° C., to produce a residual hydrocarbon vapor and a fat solvent containing absorbed vapors which consist essentially of xylenes and ethyl benzene, separating said fat solvent from said residual vapor, and fractionally distilling the separated fat solvent to recover said absorbed xylenes and ethyl benzene.

5. In a process for separating substantially pure toluene from a petroleum hydrocarbon distillate containing non-aromatic hydrocarbons and having a relatively wide boiling range above and below 110.6° C., the steps of fractionally distilling said distillate to produce a concentrate containing not less than about 5% toluene, said concentrate containing an amount of components boiling higher than about 120° C. not greater than the content of said toluene fraction in said concentrate, and a content of components boiling higher than about 125° C., being not greater than the larger of the following: 5% of said toluene content and ½% of the total concentrate, said concentrate having a true initial boiling point not higher than about 100° C., and a true final boiling point at least about 112° C., contacting said concentrate in a vapor phase with a liquid solvent selectively dissolving aromatic hydrocarbons and boiling at a temperature substantially above 110.6° C., to produce a residual hydrocarbon vapor and a fat solvent containing absorbed vapors consisting essentially of toluene, separating said fat solvent from said vapor and fractionally distilling the separated fat solvent to recover said absorbed toluene.

6. In a process for separating substantially pure toluene from a petroleum hydrocarbon distillate containing non-aromatic hydrocarbons and having a relatively wide boiling range above and below 110.6° C., the steps of fractionally distilling said distillate to produce a concentrate containing not less than about 5% toluene, said concentrate containing an amount of components boiling higher than about 120° C. not greater than the content of said toluene fraction in said concentrate, and a content of components boiling higher than about 125° C., being not greater than the larger of the following: 5% of said toluene content and ½% of the total concentrate, contacting said concentrate in a vapor phase with a liquid solvent selectively dissolving aromatic hydrocarbons and boiling at a temperature substantially above 110.6° C. and to produce a fat solvent containing absorbed vapors consisting essentially of toluene, separating said fat solvent from said vapor and fractionally distilling the separated fat solvent to recover said absorbed toluene.

7. In the process according to claim 5, the step of contacting said concentrate in the vapor phase with a mixture of alkyl phenols.

8. In the process according to claim 5, the step of contacting said concentrate in the vapor phase with nitrobenzene.

9. In a process for separating substantially pure toluene from a petroleum hydrocarbon distillate containing non-aromatic hydrocarbons and having a relatively wide boiling range above and below 110.6° C., the steps of fractionally distilling said distillate to produce a concentrate containing more than 2% of toluene, said concentrate containing an amount of components boiling higher than about 120° C. not greater than the content of toluene in said concentrate, and a content of components boiling higher than about 125° C., being not greater than the larger of the following: 5% of said toluene content and ½% of the total concentrate, said concentrate having a true initial boiling point not higher than about 100° C., and a true final boiling point of at least about 112° C., contacting said concentrate in a vapor phase with a liquid solvent selectively dissolving aromatic hydrocarbons and boiling at a temperature substantially above 110.6° C., to produce a residual hydrocarbon vapor and a fat solvent containing absorbed vapors consisting essentially of toluene, separating said fat solvent from said vapor and fractionally distilling the separated fat solvent to recover said absorbed toluene.

10. In a process for separating substantially pure toluene from a straight-run petroleum distillate having a relatively wide boiling range above and below 110.6° C., the steps of fractionally distilling said distillate to produce a concentrate containing more than 2% of toluene, said concentrate containing an amount of components boiling higher than about 120° C. not greater than the content of toluene in said concentrate, and a content of components boiling higher than about 125° C., being not greater than the larger of the following: 5% of said toluene content and ½% of the total concentrate, said concentrate having a true initial boiling point not higher than about 100° C., and a true final boiling point of at least about 112° C., contacting said concentrate in a vapor phase with a liquid solvent selectively dissolving aromatic hydrocarbons and boiling at a temperature substantially above 110.6° C., to produce a residual hydrocarbon vapor and a fat solvent containing absorbed vapors consisting essentially of toluene, separating said fat solvent from said vapor and fractionally distilling the separated fat solvent to recover said absorbed toluene.

CLARENCE L. DUNN.
ROBERT B. McCONAUGHY.